United States Patent [19]

Knoll et al.

[11] Patent Number: 4,936,849

[45] Date of Patent: Jun. 26, 1990

[54] INTRAOCULAR LENS

[75] Inventors: Randall L. Knoll, Mahtomedi; James E. Aysta, Stillwater; Wilhelm Lewon, St. Paul, all of Minn.

[73] Assignee: Minnesota Mining and Manufacturing Company, Saint Paul, Minn.

[21] Appl. No.: 168,394

[22] Filed: Mar. 15, 1988

[51] Int. Cl.$^5$ ............................................... A61F 2/16
[52] U.S. Cl. ......................................... 623/6; 29/525; 264/1.7
[58] Field of Search ...................... 623/6, 901; 264/1.1, 264/1.7; 29/525

[56] References Cited

U.S. PATENT DOCUMENTS

| | | |
|---|---|---|
| 3,758,448 | 9/1973 | Stamberger . |
| 3,822,089 | 7/1974 | Wichterle ............................ 351/160 |
| 3,850,892 | 11/1974 | Shen et al. ........................ 351/160 X |
| 3,876,581 | 4/1975 | Neogi . |
| 3,880,818 | 4/1975 | Shen et al. ........................ 351/160 X |
| 3,937,680 | 2/1976 | DeCarle ............................ 351/160 X |
| 3,991,426 | 11/1976 | Flom et al. ............................ 623/6 |
| 3,994,027 | 11/1976 | Jensen et al. ............................ 623/6 |
| 4,104,339 | 8/1978 | Fetz et al. ............................ 123/6 X |
| 4,139,915 | 2/1979 | Richards et al. ....................... 623/6 |
| 4,150,471 | 4/1979 | Richards et al. ....................... 29/450 |
| 4,155,125 | 5/1979 | Woodcock et al. ...................... 623/6 |
| 4,192,022 | 3/1980 | LaHaye ................................. 623/6 |
| 4,244,060 | 1/1981 | Woffer ................................. 623/6 |
| 4,307,043 | 12/1981 | Chase et al. .......................... 264/1.7 |
| 4,366,582 | 1/1983 | Faulkner .............................. 623/6 |
| 4,403,354 | 9/1983 | Rainin ................................. 623/6 |
| 4,473,910 | 10/1984 | Grinder ................................ 623/6 |
| 4,551,864 | 11/1985 | Akhavi ................................. 623/6 |
| 4,556,998 | 12/1985 | Siepser ................................. 623/6 |
| 4,578,078 | 3/1986 | Arkell et al. ......................... 623/6 |
| 4,580,299 | 4/1986 | Lindstrom ............................. 623/6 |
| 4,618,649 | 10/1986 | Ofstead ................................ 525/60 |
| 4,668,446 | 5/1987 | Kaplan et al. ....................... 623/6 X |
| 4,678,469 | 7/1987 | Kelman ................................. 623/6 |
| 4,702,865 | 10/1987 | Koziol et al. ........................ 624/1.7 |
| 4,781,718 | 11/1988 | Lindstrom ............................. 623/6 |
| 4,790,846 | 12/1988 | Christ et al. .......................... 623/6 |

FOREIGN PATENT DOCUMENTS

| | | |
|---|---|---|
| 0188110 | 7/1986 | European Pat. Off. . |
| 0226400 | 6/1987 | European Pat. Off. . |
| 2384490 | 10/1978 | France . |
| 2180757 | 4/1987 | United Kingdom . |

OTHER PUBLICATIONS

Allarakhia, J. Cataract Refract Surg–vol. 13, Nov. 1987, pp. 607–620.
American medical Optics–Handout (1985), "Intraocular Lens Material: Present and Future", pp. 1–19.
Encyclopedia of Chemical Technology, vol. 20–1982, pp. 922–962 and vol. 15, 273–291.
Paul Leonard et al., Lens Implantation: 30 Years of Progress, 1982, pp. 29–51.

*Primary Examiner*—Ronald L. Frinks
*Attorney, Agent, or Firm*—Wegner & Bretschneider

[57] ABSTRACT

Disclosed is an intraocular lens comprising a lens element and a plurality of haptics extending therefrom, at least one of the haptics having an anchoring filament with an enlarged complete or partial mushroom-shaped end fixedly disposed inside a passage in the lens element. Also disclosed is a method for fixing a haptic having an anchoring filament to a lens element in a soft intraocular lens comprising the steps of (a) forming in the lens element a passage having a width that is less than the greatest width of the anchoring filament, (b) lubricating the anchoring filament of the haptic, the passage in the lens element, or both, (c) inserting the anchoring filament end-first into the passage, and (d) washing the intraocular lens to remove the lubricant.

31 Claims, 2 Drawing Sheets

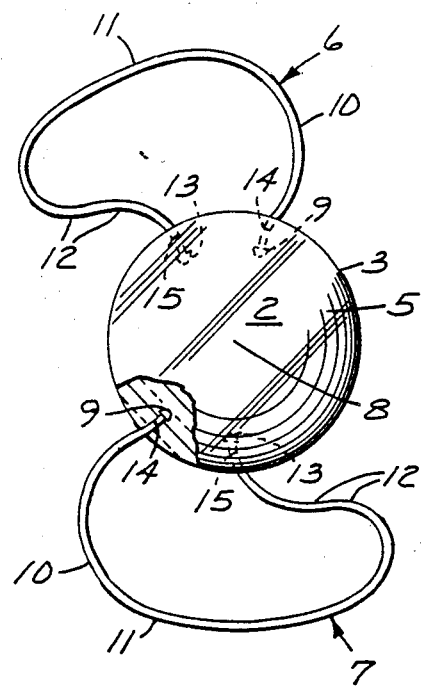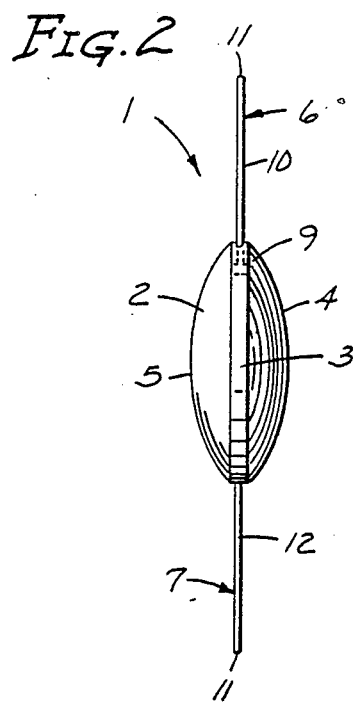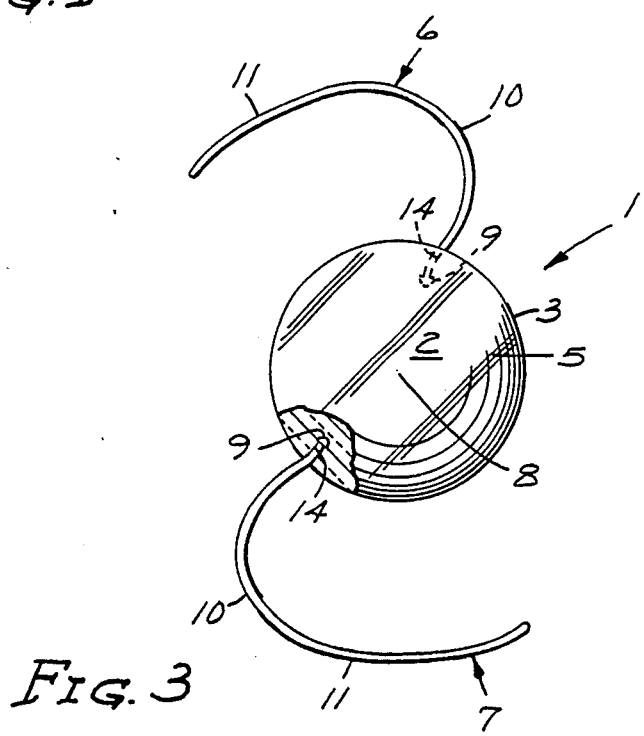

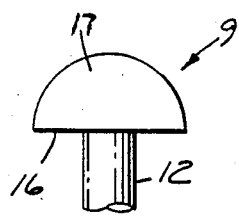
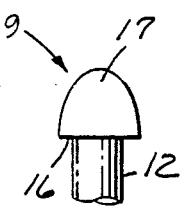
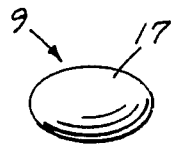
FIG. 4a    FIG. 4b    FIG. 4c
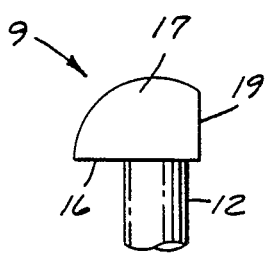
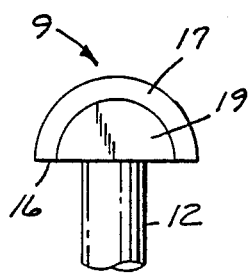
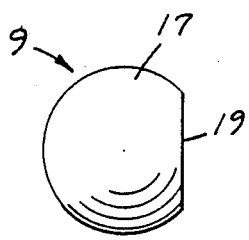
FIG. 5a    FIG. 5b    FIG. 5c
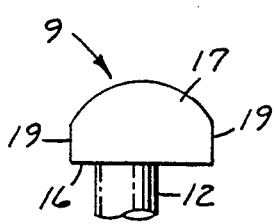
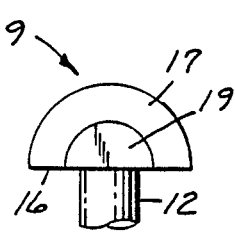
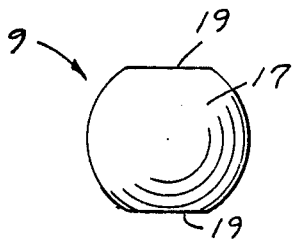
FIG. 6a    FIG. 6b    FIG. 6c
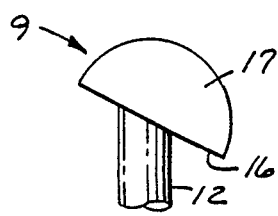
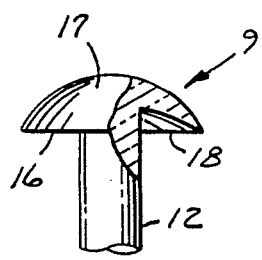
FIG. 7    FIG. 8

INTRAOCULAR LENS

This invention relates to a soft intraocular lens (IOL) useful as an artificial lens implant in the eye. In particular, it relates to a soft IOL having a haptic with an enlarged end anchored inside the lens element and a method of attachment.

Artificial intraocular lenses have been used for years in the replacement of damaged or diseased natural lenses. Typically, these lenses comprise a lens element (or refractive element) and support elements known as haptics, which maintain the lens in the correct position within the eye. An intraocular lens can be either hard or soft.

A hard intraocular lens uses a rigid polymeric or glass lens element. A soft intraocular lens uses a resilient lens element made of flexible materials, permitting dimension reduction of the element and insertion in the eye through a smaller, less traumatic incision than required for hard lenses. The pliable, compliant nature of soft lenses also causes less irritation of sensitive eye tissue than hard lenses, which can cause problems such as uveitis.

Various designs are useful for fixing haptics to the lens element of a soft intraocular lens. In some lenses the haptic and lens element are a single element. In another design the haptic has an anchoring filament fixed inside a passage in a separate lens element. In the later design difficulty inserting th anchoring filament into the passage is often encountered during manufacture. Problems also arise both during or after implanting the lens when forces acting on the haptic displace the anchoring filament from its proper position within the lens element, resulting in the anchoring filament either penetrating beyond the end of the passage into the lens material itself or pulling out of the passage entirely. Besides potentially damaging the lens, displacement of the anchoring filament can also create vision problems by causing the lens element to shift from its proper location within the eye.

Methods for inserting haptic anchoring filaments into lens elements include casting the lens with the filament in the mold, heat-staking, ultrasonic welding or staking, swelling hydratable lenses before inserting the filament into a pre-formed passage inside the lens element, and simple forceful insertion of filaments into pre-formed passages. Some of these methods can damage the lens element while others provide insufficient pull out resistance after insertion.

An objective of the present invention is to create a soft intraocular lens having a superior haptic design effecting improved fixation of the haptic to the lens element. Another objective of the present invention is to provide a method for inserting the anchoring filament of a haptic into a lens element.

Accordingly, the present invention is a soft intraocular lens comprising a lens element and a plurality of haptics extending therefrom, at least one of the haptics having an anchoring filament with an enlarged complete or partial mushroom-shaped end fixedly disposed inside a passage in the lens element. The present invention is useful as an artificial lens implant in the eye. Also according to the present invention there is a method for fixing a haptic having an anchoring filament to a lens element comprising the steps of forming in the lens element a passage having a width that is less than the greatest width of the anchoring filament, lubricating the anchoring filament of the haptic, the passage in the lens element, or both, inserting the anchoring filament end-first into the passage, and washing the intraocular lens to remove the lubricant.

FIG. 1 is a front elevation view of a preferred embodiment of the soft intraocular lens of the present invention.

FIG. 2 is a side elevation view of the preferred embodiment shown in FIG. 1.

FIG. 3 is a front elevation view of a preferred embodiment of the soft intraocular lens of the present invention.

FIGS. 4a–c, 5a–c, and 6a–c are, respectively, front, side, and top views of an enlarged mushroom-shaped end according to different embodiments of the present invention.

FIGS. 7 and 8 are side views of an enlarged mushroom-shaped end according to different embodiments of the present invention.

Referring to FIGS. 1–3, intraocular lens of the present invention 1 comprises a lens element 2 and haptics 6 and 7. Lens element 2 comprises cylindrical periphery 3, spherical posterior face 4, and spherical anterior face 5, the faces having curvatures providing optical properties depending on the needs of the patient. Haptics 6 and 7 are spring-like support loops for holding the lens in the proper position within the eye and are located in a plane common with lens element 2 and symmetrical to the geometric axis 8. Each of haptics 6 and 7 comprises arcuate support element 11 extending into anchoring filaments 10 and 12 having enlarged mushroom-shaped ends 9 and 13, which are force-fit inside passages 14 and 15 of lens element 2.

Referring to FIGS. 4–8, anchoring filament 12 terminates in mushroom-shaped end 9, having shoulder periphery 16, cap 17, shoulder region 18, and flat side 19.

The lens element useful in the intraocular lens of the present invention is made of polymeric materials well known in the manufacture of soft intraocular lenses. Materials and methods for making useful lens elements are well known, as disclosed in Allarakhia et al., "Soft Intraocular Lenses," *J Cataract Refract Surg*, 13:607–620, 1987, and Leonard, et al., *Lens Implantation*, 30 *Years of Progress*, The Hague, Dr. W. Junk Publishers, 1982. The lens element includes both the optical zone of the lens and any surrounding structure for anchoring the haptic. Preferably, the lens element is a biconvex, circular disk (FIGS. 1–3) made by grinding, lathe cutting, compression molding, injection molding, or cast molding. Other useful lens shapes include plano convex and concavo-convex, such as disclosed in U.S. Pat. No. 4,573,998, issued to Mazzocco, incorporated herein by reference, as well as aspherical and diffraction lens elements.

The lens element material is any well known material typically used in the manufacture of lens elements. Preferably, the lens element material is medical optical grade, implant quality silicone, polyurethane, or hydrogel. Examples of useful lens elements made of silicone and polyurethane are well known, such as the silicone lens elements disclosed in U.S. Pat. No. 4,702,865, issued to Koziol et al., and European Pat. No. 43640, issued to Polmanteer et al., the disclosures of which are incorporated herein by reference.

Hydrogels useful in accordance with the present invention are also well known in the manufacture of lens elements and include homopolymers and copolymers of acrylate and methacrylate esters having at least one hydroxyl group on the side chain, such as 2-hydroxyethyl methacrylate, ethylene glycol dimethacrylate, hydroxyethoxyethyl methacrylate, hydroxydiethoxy methacrylate, and glyceryl methacrylate, as well polymers and copolymers of monomers such as methoxyethoxyethyl methacrylate, methoxydiethoxyethyl methacrylate, methoxyethyl methacrylate, methacrylic acid, vinyl alcohol, vinyl acetate, and N-vinyl-2-pyrrolidone and related N-alkenyl-2-pyrrolidones. Examples of useful hydrogels are disclosed in U.S. Pat. No. 4,664,666, issued to Barrett, incorporated herein by reference. Examples of preferred hydrogel polymers are derived from poly(vinyl trifluoroacetate) copolymers such as disclosed in U.S. Pat. No. 4,618,649, issued to Ofstead, and European Patent Application No. 0 188 110, published July 23, 1986, the disclosures of which are incorporated herein by reference. Other useful hydrogels are disclosed in Wichterle, "Hydrogels," *Encyclopedia of Polymer Science and Technology*, New York, Interscience, 1971, pp. 273–290; Wichterle et al., "Hydrophilic Gels For Biological Use," *Nature*, 185: 117–118, 1960; and Ratner et al., "Synthetic Hydrogels for Biomedical Applications," *Hydrogels for Medical and Related Applications*, American Chemical Society, Washington, D.C., 1976, pp. 1–35; the disclosures of which are incorporated herein by reference. Cross-linked hydrogels ar also useful in accordance with the present invention. For example, poly(hydroxyethyl methacrylate) cross-linked with 31% ethylene dimethacrylate is a preferable cross-linked hydrogel.

The lens element used in accordance with the present invention has at least one passage, preferably blind-ended, in which the anchoring filament of the haptic is fixed. The passages are located in various positions in, and at various angles to, the lens element depending on the type of haptic support used and desired distribution of compression forces on the haptic. The position of the passage should preferably intrude as little as possible into the optical zone of the lens (i.e., the portion of the lens element that focuses light on the retina of the eye) and multiple passages should be spaced so that anchoring filaments disposed therein do not interfere with deformation of the lens element during implantation. Various examples for passage locations are disclosed in the following United States patents, the disclosures of which are incorporated herein by reference: U.S. Pat. No. 4,578,078, issued to Arkell et al.; U.S. Pat. No. 4,150,471, issued to Richards et al.; U.S. Pat. No. 4,403,354, issued to Rainin; U.S. Pat. No. 3,994,027, issued to Jensen et al.; U.S. Pat. No. 4,473,910, issued to Grinder; and U.S. Pat. No. 4,104,339, issued to Fetz et al. For example, the passages can open onto either face of the lens element or its periphery, and can be either normal to the lens surface or form an acute angle with the lens surface. Preferably, the passages are chordally located in the lens element, such as shown in FIGS. 1 and 2. The preferable method for making the passages in the lens element is drilling, although other passage forming techniques will be apparent to those of ordinary skill in the art.

The length and width of the lens element passage vary. The width of the passage is defined by an imaginary line bounded by the side walls of the passage and normal to a longitudinal line through the center of the passage. The length and width of the passage are preferably designed so that the mushroom-shaped end is force-fit inside the passage and the passage closes around the anchoring filament behind the mushroom-shaped end, allowing no gaps between the anchoring filament and the passage walls at the entrance to the passage. Accordingly, the width/length ratio of the passage is preferably at least ⅛, more preferably between 1/6 and 1/10 , and most preferably about ⅛. Also accordingly, the passage length is preferably between 3.0 and 10.0, more preferably between 4.0 and 6.0 , times the width of the mushroom-shaped end, i.e., the greatest dimension of the mushroom-shaped end normal to the filament axis, and preferably part, more preferably all, of the width along the length of each passage is less than, more preferably between 0.2 and 0.9 times, most preferably between 0.3 and 0.7 times, the width of the enlarged mushroom-shaped end at its shoulder, e.g., for a mushroom-shaped end with a circular shoulder periphery, the diameter of the shoulder periphery. The width of the passage can be less than the width of the anchoring filament as well as the diameter of its enlarged end. When a hydrogel is used, the width of the passage is determined when the lens element is hydrated although the passage is preferably formed when the lens element is dry.

The passage of the lens element can be straight or curved, can have a constant or variable cross-section throughout its length, and the cross-section can be completely curvilinear, e.g., a circle or ellipse; partly curvilinear, e.g., an arc connected by one or more straight sides; or three or more sided, e.g., a quadrangle or hexagon. Preferably, the passage is straight and cylindrical.

Although the passage is preferably designed so that the mushroom-shaped end is force-fit inside the passage, the mushroom-shaped end can also be fixed inside the passage by other known means, for example, by using adhesives or ferrules inside the passage.

At least one of the haptics useful in accordance with the present invention comprises an anchoring filament fixed to any known support element for maintaining the lens element in the correct position within the eye. Such support elements include one and multi-part haptics and can form a single structure with the anchoring filament.

The support element of the haptic is formed as a plate, arm, loop, leg, or other known support structure, such as disclosed in the previously cited U.S. Pat. No. 4,578,078, issued to Arkell et al.; U.S. Pat. No. 4,150,471, issued to Richards et al.; U.S. Pat. No. 4,403,354, issued to Rainin; U.S. Pat. No. 3,994,027, issued to Jensen et al.; U.S. Pat. No. 4,473,910, issued to Grinder; and U.S. Pat. No. 4,104,339, issued to Fetz et al., as well as the following United States patents, the disclosures of which are also incorporated herein by reference: U.S. Pat. No. 4,092,743, issued to Kelman and U.S. Pat. No. 4,110,848, issued to Jensen. Optimum design of the support element is often determined by the location of the implant within the eye, e.g., the anterior or posterior chamber, and the method of attachment to the eye tissue, e.g., spring force exerted by the haptic against the equatorial region of the lens capsule, ciliary sulcus, or anterior angle.

The anchoring filament of the haptic has an enlarged complete or partial mushroom-shaped end, i.e., an enlarged end having a shoulder region at least part of which extends radially from the filament at an angle no greater than about 90° and a complete or partial spherical or aspherical dome-shaped cap connected to the periphery of the shoulder region. Typical angles between the filament and the shoulder region include angles up to 35°, 45°, 65°, 80°, and 90°. Such angles permit the shoulder region to act like a barb or hook, resisting pull-out from the lens element.

The mushroom-shaped end can be centered on the anchoring filament, i.e., share the same longitudinal axis (FIGS. 4a–c), or off-centered (FIGS. 6a–c). The mushroom-shaped end can also be tilted with respect to the anchoring filament, i.e., the longitudinal axis of the mushroom-shaped end is not parallel to the longitudinal axis of the anchoring filament (FIG. 7).

The shoulder periphery is preferably a complete or partial circle or ellipse; a complete circle or ellipse forms a complete mushroom-shaped end and a partial circle or ellipse forms a partial mushroom-shaped end. A complete mushroom-shaped end having an elliptical shoulder periphery (FIGS. 4a–c) is slightly flattened on two sides, adding additional torsional rotation stability to the anchoring filament. A partial mushroom-shaped end having a partial circle shoulder periphery can have a flat surface on one side of the cap (FIGS. 5a–c), or both sides of the cap (FIGS. 6a–c), which also resists rotation of the filament within the passage.

In one embodiment, the enlarged mushroom-shaped end has a circular periphery connected to a spherical dome-shaped cap, i.e., in mathematical terms, a single base spherical segment (FIG. 7). For example, the enlarged mushroom-shaped end is hemispherical. Preferably, the shoulder region is slightly cupped (FIG. 8).

The size of both the anchoring filament and mushroom-shaped end vary. Preferably, the transverse width of the filament itself is between about 0.05 and 0.3 mm, more preferably between about 0.12 and 0.17 mm. The mushroom-shaped end has a preferable shoulder width (i.e., the greatest transverse dimension of the shoulder periphery) between about 0.1 and 0.6 mm, more preferably between about 0.2 and 0.35 mm, and a cap height (i.e., distance between the shoulder periphery and the top of the cap) between about 0.04 and 0.4 mm, more preferably about 0.1 and 0.15 mm.

Preferably, the haptic used in accordance with the present invention is a spring-like support loop, wherein the anchoring filament is merely an extension of the loop. Such spring-like support loops can be co-planar with the lens element, angled, or vaulted, and have opposing enlarged mushroom-shaped ends forming a closed loop (FIGS. 1 and 2), or have only one enlarged mushroom-shaped end and anchoring filament fixed inside the lens element and form an open loop, i.e., one end of the loop is not fixed to the lens element (FIG. 3). The curved shape of the loop preferably matches the shape of the eye tissue that supports the lens after implantation. Accordingly, such a support loop extending radially from the lens element is resiliently compressed against the eye tissue after implanting, and as such is somewhat self-adjusting, allowing easy accurate positioning within the eye.

As long as at least one of the haptics in the soft intraocular lens of the present invention has an anchoring filament having an enlarged mushroom-shaped end fixed inside the lens element according to the present invention, the remaining haptic or haptics can be any known haptic for soft intraocular lenses, such as described in the heretofore mentioned patents and publications. Preferably, all haptics in the soft intraocular lens of the present invention are attached to the lens element by the anchoring filament of the present invention.

The dome shape of the cap of the mushroom-shaped end facilitates distribution of stress against the side and end walls of the passage in the lens element by increasing the surface area of the fixation interface, which hinders penetration of the head into the lens element material beyond the end of the passage. Such stress occurs during implantation within the eye when the lens is deformed to fit through a narrow surgical incision and because the lens element is maintained in proper position within the eye due to pressure exerted by the spring-like loops against both the lens element and surrounding eye tissue. The shoulder of the mushroom-shaped end acts like a barb or hook, providing resistance against force acting to pull the filament from the passage. The possibility of unwanted shifting of the lens element within the eye, possible damage to the optical zone of the lens element, or both is thereby reduced.

The haptic material, including the anchoring filament and enlarged mushroom-shaped end, is rigid, flexible, or resilient and includes biocompatible polymers, such as polypropylene, polymethyl methacrylate, polyimide, polyethylene, polytetrafluoroethylene, polyamide (nylon), and polyethylene terephthalate, or metals, such as platinum/iridium alloys, stainless steel, and titanium. Preferably, the haptic is polypropylene, polyimide, or polymethyl methacrylate. Preferably, the anchoring filament material is a biocompatible axially oriented polymer. These and other exemplary materials are disclosed in the heretofore mentioned patents and publications.

The haptic is made by methods well known to those of ordinary skill in the art, such as molding, extruding, or machining. Preferably, the enlarged mushroom-shaped end is formed by heat-treatment of a non-enlarged end of the anchoring filament that is made of axially oriented polymer.

The anchoring filament is placed inside the passage in the lens element by simply inserting the filament into the passage until the desired position within the passage is attained. Preferably, the anchoring filament, the lens element passage, or both are lubricated before the filament is inserted into the passage. The lens is thereafter washed to remove the lubricant. When washes other than water are necessary to remove the lubricant, residual wash is removed.

Useful lubricants are preferably non-reactive with the intraocular lens components. Useful lubricants include organic solvents, surfactants, oils, greases and solid lubricants. Examples of useful lubricants are surfactants, such as ionic and non-ionic detergents and materials such as sodium oleate, sodium lauryl sulfate, polyethylene glycol, polyvinyl alcohol, and linear alkyl sulfonates, water-soluble soaps that are the reaction products of sodium or potassium and long chain fatty acids such as Castile soap and liquid green soap, pure petroleum lubricants such as normal, iso-, and cycloparaffins, monoaromatics, which contain saturated rings as well as saturated side chains, and substituted polyaromatics, boundary lubricants such as palm oil, olive oil, and cotton seed oil, $C_1$-$C_4$ alcohols, water miscible solvents, and polymers of ethylene and propylene oxides, water or alcohol-soluble greases such as petroleum jelly, which typically contain a thickening (or gelling) agent, such as sodium or calcium salt of oleic, palmitic, stearic, or other carboxylic acid derived from animal, fish, and vegetable oils, in a liquid lubricant. Preferred lubricants are mixtures of water and alcohols, such as ethyl, methyl, and iso-propyl alcohol.

Useful washes include solvents that will solvate the lubricant used without damaging or degrading the intraocular lens components. Examples of preferred useful washes are water and alkyl alcohols having up to eight carbon atoms. Use of washes other than purified water requires that the wash used be removed from the intraocular lens before use as an implant.

The method of the present invention is useful for inserting haptic anchoring filaments of various designs not presently claimed into various lens elements, for example, as described in the heretofore mentioned United States Patents.

Methods and equipment useful for implanting the soft intraocular lens of the present invention into the eye are well known, as shown in Allarakhia et al., "Soft intraocular lenses," *J Cataract Refract Surg*, VOL 13, November, 1987, Leonard et al., *Lens Implantation, 30 Years of Progress*, Dr.W. Junk Publishers, The Hague, 1982, and U.S. Pat. No. 4,556,998, issued to Siepser.

The following non-limiting examples illustrate the present invention. All parts and percentages are by weight unless indicated otherwise.

EXAMPLE 1

A mixture of 22 parts of 2-hydroxyethyl methacrylate, 0.6 parts allyl methacrylate, 11 parts N-vinyl-2-pyrrolidone, and 0.1 parts azobisisobutyronitrile, filtered and degassed under vacuum and sealed in a low density polyethylene tube, is polymerized by heating in a cycle of 40 hrs at 40° C., 6 hrs at 60° C., and 16 hrs at 90° C. After being allowed to cool slowly at room temperature, a 2.0 mm thick button cut from the 12.7 mm diameter rod of polymerized material is placed in a vacuum chuck and rough turned to a diameter of 4.3 mm using an Enco lathe equipped with a 0.5 mm radius diamond tool. The 4.3 mm diameter button is placed in a split-ring collet with a seat diameter of 4.3 mm and lathed with a Pal lathe using a 0.05 mm radius diamond tool (available from A. A. Machinery Repair, Wayne, N.J.) to obtain a convex surface having a 4.07 mm radius of curvature on one face of the button, and the procedure is repeated for the other lens face to create a biconvex lens element.

Opposing pairs of passages having a diameter of 0.09 mm and a depth of 0.7 mm are drilled into the cylindrical surface of the lens element, one hole of each pair is normal to the surface and the other is drilled at an angle of 27.5 degrees such that the center distance between the holes of each pair is 0.9 mm, using a Servo Computer Numerically Controlled Drilling Machine equipped with a Quincy Stepper Driver and a 0.09 mm diameter cobalt drill having a flute length of 0.7 mm (manufactured by Gunther and Co., Frankfurt am Main, Federal Republic of Germany). The lens element is then ultrasonically cleaned by immersion in trichlorotrifluoroethane for 30 seconds and again for one minute, and then dried for ten seconds under a nitrogen gas jet.

A polypropylene haptic loop having a diameter of 0.15 mm and ends about 0.9 mm apart is mounted on a slide opposite an Ogden Mighty Watt Block Heater (Model MW-215, 110–120 volt, 150 watt, 0.312 inch diameter, 2 inches long). The heater is mounted in a brass heat sink from which two 0.045 inch diameter brass formed wires extend toward the slide. The wires are heated to 550° F., and the loop ends are moved to within 0.004 inches of the wires until a mushroom-shaped head having a diameter of 0.28 mm and a height of 0.15 mm is formed on each end of the loop. An identical loop is likewise treated.

The lens element is hydrated by immersion in non-pyrogenic sterile water for irrigation for about 15 hours in a sealed container. Placed on a vacuum pedestal under a microscope, the passages in the hydrated lens are lubricated by spraying with ethanol using an aerosol applicator, and the two mushroom-shaped ends of one of the haptics are inserted into one of the passage pairs. The procedure is repeated for the other haptic with the other passage pair.

The lens is then washed by immersion in sterile water maintained at about 65° C. for 3.5 hours. The washing procedure is repeated three times. The lens is then dried and cooled by standing at about 20° C. for 14 hours.

EXAMPLE 2

A lens element is cut and shaped as in Example 1 from a polymerized rod as in Example 1 from the following composition: 10 parts pentafluorostyrene, 17.6 parts methyl methacrylate, 0.2 parts diallyl phthalate, 0.2 parts diallyl maleate, 7 parts of purified cellulose acetate acrylate (MW=50,000; degree of unsaturation=1/1000), 165 parts of N-vinyl-2-pyrrolidone, and 0.4 parts azobisisobutyronitrile. Polypropylene haptics are prepared and inserted into the lens element as in Example 1.

EXAMPLE 3

A lens element is cut and shaped as in Example 1 from a rod containing a polymerized mixture as in Example 1 of 10 parts pentafluorostyrene, 13.6 parts methyl methacrylate, 0.2 parts diallyl phthalate, 0.2 parts diallyl maleate, 2 parts of Scott-Bader Crystic 181LV, a commercial, clear isophthalate based polyunsaturated polyester resin (which contains 36% styrene; MW=3,500; degree of unsaturation=1/363) and 7 parts of cellulose acetate acrylate, 167 parts N-vinyl-2-pyrrolidone, and 0.4 parts azobisisobutyronitrile. Polypropylene haptics are prepared and inserted into the lens element as in Example 1.

EXAMPLE 4

A lens element is cut and shaped as in Example 1 from a rod polymerized as in Example 1 having the following composition: 1.6 parts pentafluorostyrene, 3.3 parts methyl methacrylate, 0.02 parts diallyl phthalate, 0.02 parts diallyl maleate, 0.06 parts ethyoxylated bisphenol A dimethacrylate, 0.8 parts of the isophthalate-based polyunsaturated polyester resin referred to in Example 3 and 0.8 parts cellulose acetate methacrylate (MW=50,000; degree of unsaturation=1/1000) 33.4 parts of N-vinyl-2-pyrrolidone, and 0.08 parts azobisisobutyronitrile. Polypropylene haptics are prepared and inserted into the lens element as in Example 1.

EXAMPLE 5

A lens element is cut and shaped as in Example 1 from a rod polymerized as in Example 1 having the following composition: pentafluorostyrene, 3.5 parts methyl methacrylate, 0.1 part diallyl phthalate, 0.75 parts of the isophthalate-based polyunsaturated polyester resin referred to in Example 3, 1.5 parts of cellulose acetate methacrylate of Example 4, 0.05 parts of 4-benzoyl-3-hydroxyphenyl methacrylate, 43.1 parts of N-vinyl-2-pyrrolidone, and 0.1 parts of azobisisobutyronitrile. Polypropylene haptics are prepared and inserted into the lens element as in Example 1.

EXAMPLE 6

A lens element is cut and shaped as in Example 1 from a rod polymerized as in Example 1 having the following composition: 6 parts methylmethacrylate, 0.1 parts diallyl phthalate, 0.75 parts of the polyunsaturated polyester resin in Example 3, 1.5 parts of cellulose acetate methacrylate of Example 4, 41.65 parts of N-vinyl-2-pyrrolidone, and 0.1 parts of azobisisobutyronitrile. Polypropylene haptics are prepared and inserted into the lens element as in Example 1.

EXAMPLE 7

A lens element is cut and shaped as in Example 1 from a rod polymerized as in Example 1 having the following composition: 1.12 parts of the solid isophthalate based polyunsaturated polyester resin referred to in Example 3, 14 parts freshly distilled methyl methacrylate, 0.15 parts ethoxylated bisphenol A dimethacrylate, 0.1 parts diallyl maleate, 1.25 parts 2-hydroxyethylmethacrylate, 0.75 parts cellulose acetate methacrylate of Example 4, 0.12 parts diacetone acrylamide, 32.51 parts of N-vinyl-2-pyrrolidone, and 0.1 parts of azobisisobutyronitrile. Polypropylene haptics are prepared and inserted into the lens element as in Example 1.

EXAMPLE 8

A lens element is cut and shaped as in Example 1 from a rod polymerized as in Example 1 having the following composition: 1.12 parts of the solid isophthalate-based polyunsaturated polyester resin of Example 7, 13.96 parts methyl methacrylate, 0.15 parts ethoxylated bisphenol A dimethacrylate, 0.1 parts diallyl maleate, 1.25 parts 2-hydroxyethyl methacrylate, 0.75 parts cellulose acetate methacrylate of Example 4, 0.12 parts diacetone acrylamide, 0.05 parts 4-benzoyl-3-hydroxyphenyl methacrylate, 32.5 parts of N-vinyl-2-pyrrolidone, and 0.1 parts of azobisisobutyronitrile. Polypropylene haptics are prepared and inserted into the lens element as in Example 1.

EXAMPLE 9

A lens element is cut and shaped as in Example 1 from a rod that is polymerized mixture of the following composition: 0.75 parts of the purified cellulose acetate methacrylate of Example 4, 0.5 parts of crystallized diacetone acrylamide, 12.6 parts of methyl methacrylate, 0.15 parts ethoxylated bisphenol A dimethacrylate, 0.13 parts polyethylene glycol dimethacrylate, 0.12 parts allyl methacrylate, 5 parts 2-hydroxyethyl methacrylate, 30.75 parts of N-vinyl-2-pyrrolidone. The mixture is polymerized by a dose of 2.5 MegaRads of ionizing radiation from a Cobalt 60 source. Polypropylene haptics are prepared and inserted into the lens element as in Example 1.

EXAMPLE 10

A lens element is cut and shaped as in Example 1 from a rod polymerized as in Example 1 having the following composition: 0.48 parts of the isophthalate based polyunsaturated polyester resin of Example 3, 0.27 parts styrene, 20 parts 2-hydroxyethyl methacrylate, 8.95 parts methyl methacrylate, 0.1 parts ethoxylated bisphenol A dimethacrylate, 0.1 parts diallyl phthalate, 0.1 parts diallyl maleate, 1 part purified diacetone acrylamide, 19 N-vinyl-2-pyrrolidone, and 0.1 parts of azobisisobutyronitrile. Polypropylene haptics are prepared and inserted into the lens element as in Example 1.

EXAMPLE 11

A lens element is cut and shaped as in Example 1 from a rod polymerized as in Example 9 having the following composition: 2.5 parts of pentafluorostyrene, 47.25 parts 2-hydroxyethyl methacrylate, 0.25 parts of allyl methacrylate, and 0.1 parts of azobisisobutyronitrile. Polypropylene haptics are prepared and inserted into the lens element as in Example 1.

EXAMPLE 12

A lens element is cut and shaped as in Example 1 from a rod polymerized as in Example 1 having the following composition: 12.6 parts of methyl methacrylate, 0.15 parts ethoxylated bisphenol A dimethacrylate, 0.13 parts polyethylene glycol dimethacrylate, 0.12 parts allyl methacrylate, 5.0 parts 2-hydroxyethyl methacrylate, 0.75 parts of the purified cellulose acetate methacrylate of Example 4, 0.5 parts diacetone acrylamide, 30.75 parts of N-vinyl-2-pyrrolidone, and 0.1 part of azobisisobutyronitrile. Polypropylene haptics are prepared and inserted into the lens element as in Example 1.

EXAMPLE 13

A lens element is cut and shaped as in Example 1 from a rod polymerized as in Example 1 having the following composition: 15.375 parts methyl methacrylate, 0.15 parts ethoxylated bisphenol A dimethacrylate, 0.125 parts polyethylene glycol dimethacrylate, 0.125 parts allyl methacrylate, 1.25 parts 2-hydroxyethyl methacrylate, 0.75 parts of the purified cellulose acetate methacrylate of Example 4, 0.125 parts diacetone acrylamide, 32.1 parts of N-vinyl-2-pyrrolidone, and 0.1 parts of azobisisobutyronitrile. Polypropylene haptics are prepared and inserted into the lens element as in Example 1.

EXAMPLE 14

A lens element is cut and shaped as in Example 1 from a rod polymerized as in Example 1 having the following composition: 99.06 parts 2-hydroxyethyl methacrylate, 0.63 parts 4-benzoyl-3-hydroxyphenyl methacrylate, and 0.31 parts allyl methacrylate. Polypropylene haptics are prepared and inserted into the lens element as in Example 1.

EXAMPLE 15

A lens element is cut and shaped as in Example 1 from a rod polymerized as in Example 1 having the following composition: 88.06 parts 2-hydroxyethyl methacrylate, 0.56 parts 4-benzoyl-3-hydroxyphenyl methacrylate, 0.28 parts allyl methacrylate, and 11.10 parts N-vinyl-2-pyrrolidone. Polypropylene haptics are prepared and inserted into the lens element as in Example 1.

EXAMPLE 16

A lens element is cut and shaped as in Example 1 from a rod polymerized as in Example 1 having the following composition: 88.06 parts 2-hydroxyethyl methacrylate, 0.56 parts 4-benzoyl-3-hydroxyphenyl methacrylate, 0.28 parts allyl methacrylate, and 11.10 parts N,N-dimethylaminoethyl methacrylate. Polypropylene haptics are prepared and inserted into the lens element as in Example 1.

EXAMPLE 17

A lens element is cut and shaped as in Example 1 from a rod polymerized as in Example 1 having the following composition: 88.06 parts 2-hydroxyethyl methacrylate, 0.56 parts 4-benzoyl-3-hydroxyphenyl methacrylate, 0.28 parts allyl methacrylate, and 11.10 parts diacetone acrylamide. Polypropylene haptics are prepared and inserted into the lens element as in Example 1.

EXAMPLE 18

A lens element is cut and shaped as in Example 1 from a rod polymerized as in Example 1 having the following composition: 88.06 parts 2-hydroxyethyl methacrylate, 0.56 parts 4-benzoyl-3-hydroxyphenyl methacrylate, 0.28 parts allyl methacrylate, 5.55 parts N,N-dimethylaminoethyl methacrylate, and 5.55 parts diacetone acrylamide. Polypropylene haptics are prepared and inserted into the lens element as in Example 1.

EXAMPLE 19

Various lubricants are used to insert the haptic into the lens element. Lens elements and polypropylene haptics are prepared using procedures described in Example 1. The mushroom shaped heads are all in the range of 0.17 to 0.35 mm in diameter. The lens elements are hydrated as described in Example 1 and mounted on a vacuum pedestal. Lubricant is applied to the edge of the passage in the lens element and the haptic is dipped in the lubricant. The haptic is then inserted into the lens element and the ease of insertion evaluated quantitatively on a scale of 1-4, with 1 being the most difficult. The results are recorded in Table 1.

TABLE 1

| Lubricant | Ease Of Insertion |
|---|---|
| sodium lauryl sulfate | 4 |
| polysorbate 80 | 3-4 |
| soft lens detergent[1] | 3-4 |
| soft lens wetting agent[2] | 4 |
| polyvinyl alcohol | 2 |
| water-soluble gel[3] | 4 |
| petroleum jelly | 2 |
| olive oil | 2 |
| mineral oil | 2 |
| polydimethylsiloxane emulsion | 2 |
| ethanol | 4 |
| control - no lubricant | 1 |

[1]Available from Allergan Corp. as LC-65.
[2]Available from Allergan Corp. as "Hydrocare" ™.
[3]Available from Johnson & Johnson as K-Y Jelly.

EXAMPLE 20

Lens elements and haptics are prepared as in Example 1, with the exception that only one mushroom-shaped end is formed on each haptic. Dimensions of the mushroom-shaped ends of the haptics along with the filament diameter of the haptic are recorded in Table 2.

TABLE 2

| Haptic | Filament Diameter(mm) | Mushroom Diameter(mm) | Mushroom Height(mm) |
|---|---|---|---|
| 1 | 0.15 | 0.28 | 0.14 |
| 2 | 0.14 | 0.24 | 0.11 |
| 3 | 0.15 | 0.27 | 0.13 |
| 4 | 0.14 | 0.26 | 0.12 |

What is claimed is:

1. An intraocular lens comprising a lens element and a plurality of haptics extending therefrom, at least one haptic comprising a support element attached to an anchoring filament having at least one enlarged complete or partial mushroom-shaped end having a shoulder region fixedly disposed against relative movement inside a passage in the lens element.

2. The intraocular lens of claim 1 wherein the support element comprises a curved resilient filament coextensive with the anchoring filament, the passage is blind-ended, and the width of the shoulder region of the enlarged complete or partial mushroom-shaped end is greater than the width of the passage within which it is fixed.

3. The intraocular lens of claim 2 wherein the passage is cylindrical and chordally located in the lens element.

4. The intraocular lens of claim 2 wherein the width of the passage is between 0.3 and 0.7 times the width of the enlarged complete or partial mushroom-shaped end fixed therein.

5. The intraocular lens of claim 2 wherein the anchoring filament has an enlarged complete mushroom-shaped end.

6. The intraocular lens of claim 5 wherein the mushroom-shaped end has a circular shoulder periphery.

7. The intraocular lens of claim 5 wherein the mushroom-shaped end has an elliptical shoulder periphery.

8. The intraocular lens of claim 5 wherein the mushroom-shaped end is hemispherical.

9. The intraocular lens of claim 2 wherein the anchoring filament has an enlarged partial mushroom-shaped end.

10. The intraocular lens of claim 2 wherein the enlarged mushroom-shaped end has a cupped shoulder region.

11. The intraocular lens of claim 2 wherein the lens element material is a hydrogel.

12. The intraocular lens of claim 11 wherein the hydrogel comprises a homopolymer or copolymer of N-vinyl-2-pyrrolidone.

13. The intraocular lens of claim 2 wherein the lens element material is a silicone.

14. The intraocular lens of claim 2 wherein the haptic material is a biocompatible axially oriented polymer.

15. The intraocular lens of claim 14 wherein the enlarged mushroom-shaped end is formed by heat treatment of a non-enlarged end of the anchoring filament.

16. The intraocular lens of claim 2 wherein the enlarged mushroom-shaped end is formed by molding.

17. The intraocular lens of claim 2 wherein the haptic material is a biocompatible metal.

18. The intraocular lens of claim 2 wherein each haptic has two opposing enlarged mushroom-shaped ends each fixedly disposed inside a passage in the lens element.

19. A haptic comprising a support element attached to at least one anchoring filament having a width between 0.05 mm and 0.3 mm, the anchoring filament having an enlarged complete or partial mushroom-shaped end.

20. The haptic of claim 19 wherein the support element comprises a curved resilient filament co-extensive with the anchoring filament.

21. The haptic of claim 20 having two anchoring filaments co-extensive with the curved resilient filament at opposing ends thereof.

22. The haptic of claim 20 having an enlarged complete mushroom-shaped end.

23. The haptic of claim 22 wherein the mushroom-shaped end has a circular shoulder periphery.

24. The haptic of claim 22 wherein the mushroom-shaped end has an elliptical shoulder periphery.

25. The haptic of claim 22 wherein the haptic material is a biocompatible axially oriented polymer.

26. The haptic of claim 25 wherein the enlarged complete or partial mushroom-shaped end is formed by heat treatment of the end of the anchoring filament.

27. The haptic of claim 20 having an enlarged partial mushroom-shaped end.

28. The haptic of claim 20 wherein the haptic material is a biocompatible metal.

29. The haptic of claim 20 wherein the enlarged complete or partial mushroom shaped end is formed by molding.

30. A lens element for an intraocular lens comprising a refractive disk having at least one pre-formed cylindrical blind-ended passage with a width less than about 0.1 mm and a width/depth ratio of at least about ½.

31. The lens element of claim 30 wherein the width/depth ratio is between about 1/6 and 1/10.

* * * * *